US 8,705,865 B2

(12) United States Patent
Suzuki (10) Patent No.: US 8,705,865 B2
(45) Date of Patent: Apr. 22, 2014

(54) IMAGE ANALYSIS METHOD AND IMAGE ANALYSIS APPARATUS (75) Inventor: Akemi Suzuki, Kokubunji (JP)

(73) Assignee: Olympus Corporation, Tokyo (JP)

(*) Notice: Subject to any disclaimer, the term of this patent is extended or adjusted under 35 U.S.C. 154(b) by 161 days.

(21) Appl. No.: 13/445,332

(22) Filed: Apr. 12, 2012

(65) Prior Publication Data

US 2012/0201463 A1    Aug. 9, 2012

Related U.S. Application Data (63) Continuation of application No. PCT/JP2010/068191, filed on Oct. 15, 2010.

(30) Foreign Application Priority Data

Oct. 15, 2009    (JP) ................................ 2009-238441

(51) Int. Cl.
    *G06K 9/46*    (2006.01)
    *G06K 9/66*    (2006.01)
(52) U.S. Cl.
    USPC ......................................................... 382/192
(58) Field of Classification Search
    None
    See application file for complete search history.

(56) References Cited

U.S. PATENT DOCUMENTS

| | | | | |
|---|---|---|---|---|
| 5,412,468 A | * | 5/1995 | Lundberg et al. | 356/326 |
| 5,706,083 A | * | 1/1998 | Iida et al. | 356/328 |
| 6,980,294 B2 | * | 12/2005 | Namba et al. | 356/318 |
| 7,355,701 B2 | * | 4/2008 | Ishibashi | 356/300 |
| 7,605,918 B2 | * | 10/2009 | Dalrymple | 356/326 |
| 2008/0306713 A1 | * | 12/2008 | Suzuki | 702/189 |

FOREIGN PATENT DOCUMENTS

| | | |
|---|---|---|
| JP | 09-093588 | 4/1997 |
| JP | 2004-108892 | 4/2004 |
| JP | 2006-078377 | 3/2006 |
| JP | 2007-215930 | 8/2007 |
| JP | 2008-276191 | 11/2008 |
| JP | 2010-217761 | 9/2010 |
| JP | 2010-237116 | 10/2010 |
| WO | WO 2004/072624 | 8/2004 |
| WO | WO 2008/087869 | 7/2008 |

OTHER PUBLICATIONS

International Search Report, issued in corresponding International Patent Application No. PCT/JP2010/068191.

(Continued)

*Primary Examiner* — Samir Ahmed
(74) *Attorney, Agent, or Firm* — Kenyon & Kenyon LLP (57) ABSTRACT An image analysis method includes acquiring an image of an observation region including a plurality of pixels respectively having a plurality of time serially acquired data, setting an analysis region on the image of the observation region, setting a sub analysis region smaller than the analysis region, intermittently moving the sub analysis region in increments of a pixel interval over the entire analysis region, executing correlation analysis using data of pixels in the sub analysis region every time the sub analysis region is moved, so as to estimate at least a molecular number or a diffusion constant of the sub analysis region, and forming a molecular number or diffusion constant image by mapping the molecular numbers or the diffusion constants.

24 Claims, 8 Drawing Sheets

(56) References Cited

OTHER PUBLICATIONS

M. Digman, et al., "*Fluctuation Correlation Spectroscopy with a Laser-Scanning Microscope: Exploiting the Hidden Time Structure*," Biophysical Journal: Biophysical Letters L33-L36 (2005).

M. Digman, et al., "*Measuring Fast Dynamics in Solutions and Cells with a Laser Scanning Microscope*," Biophysical Journal 89: 1317-1327 (2005).

International Preliminary Report on Patentability, dated May 24, 2012, issued in corresponding International Application No. PCT/JP2010/1068191.

K. Schaetzel, "*New Concepts in Correlator Design*," Inst. Phys. Conf. Ser. No. 77, p. 175-184 (1985).

Office Action recieved in JP Application No. 2009-328441, mailed on Dec. 17, 2013, English-language translation provided.

\* cited by examiner

IMAGE ANALYSIS METHOD AND IMAGE ANALYSIS APPARATUS

CROSS-REFERENCE TO RELATED APPLICATIONS

This application is a Continuation Application of PCT Application No. PCT/JP2010/068191, filed Oct. 15, 2010 and based upon and claiming the benefit of priority from prior Japanese Patent Application No. 2009-238441, filed Oct. 15, 2009, the entire contents of all of which are incorporated herein by reference.

BACKGROUND OF THE INVENTION

1. Field of the Invention

The present invention relates to an image analysis method and image analysis apparatus.

2. Description of the Related Art

Conventionally, an image analysis method called FCS (Fluorescent Correlation Spectroscopy) is known. The FCS is described in, for example, "New Concept in Correlator Design", Klaus Sch tzel, Inst. Phys. Conf. Ser. No. 77, P175, 1985. In the FCS, one or a plurality of measurement points in a sample are intermittently irradiated with excitation light for a certain period of time (for example, 10 sec), and intensity fluctuations of fluorescence emitted from the measurement points are detected to execute correlation analysis, thereby estimating molecular numbers and diffusion constants.

Also, an image analysis method called RICS (Raster Image Correlation Stereoscopy) is known. The RICS is described in, for example, "Measuring Fast Dynamics in Solutions and Cells with a Laser Scanning Microscope", Michelle A. Digman, Claire M. Brown, Parijat Sengupta, Paul W. Wiseman, Alan R. Horwitz, and Enrico Gratton, Biophysical Journal, Vol. 89, P1317 1327, August 2005. In the RICS, a fluorescent image is acquired by detecting fluorescence generated while raster-scanning excitation light with respect to a sample. Data of each pixel in the fluorescent image represents information of an intensity of fluorescence generated from a corresponding point in the sample. That is, pixel data respectively have different acquisition times and acquisition positions. By executing spatial correlation analysis using pixel data, diffusion constants and molecular numbers are calculated.

It is preferable to form an image by mapping pieces of information obtained from a large number of measurement points of a sample so as to examine these pieces of information in association with positions in the sample.

When measurements are done using the FCS by setting a large number of measurement points on a sample, and measurement results are mapped, a time difference between the first and last measurement points is large, and mapping results include large errors due to the influence of temporal changes, and lack reliability. For example, when molecular numbers or diffusion constants are to be mapped for 256×256 measurement points, assuming that a time required to obtain a molecular number or diffusion constant per measurement point is 10 sec, a long measurement time of 256×256×10 sec is required. Even when measurement results having such long temporal differences are mapped, the mapping results become insignificant in practice.

In the RICS, although pieces of information are obtained from a large number of points in a sample, one information (for example, a molecular number or diffusion constant) per image is merely calculated in general. That is, the RICS naturally does not acquire a plurality of pieces of information from a scanning region. For this reason, the RICS does not consider mapping of acquired information.

BRIEF SUMMARY OF THE INVENTION

An object of the present invention is to provide a novel image analysis method of the RICS to calculate and map a plurality of pieces of information from a scanning region.

An image analysis method according to the present invention comprises acquiring an image of an observation region including a plurality of pixels respectively having a plurality of time serially acquired data, setting an analysis region on the image of the observation region, setting a sub analysis region smaller than the analysis region, intermittently moving the sub analysis region in increments of a pixel interval over the entire analysis region, executing correlation analysis using data of pixels in the sub analysis region every time the sub analysis region is moved, so as to estimate at least a molecular number or a diffusion constant of the sub analysis region, and forming a molecular number or diffusion constant image by mapping the molecular numbers or the diffusion constants.

According to the present invention, an image analysis method of the RICS to map and display molecular numbers or diffusion constants is provided.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention will be described hereinafter with reference to the drawings.

[Apparatus Arrangement]

Figure 1:
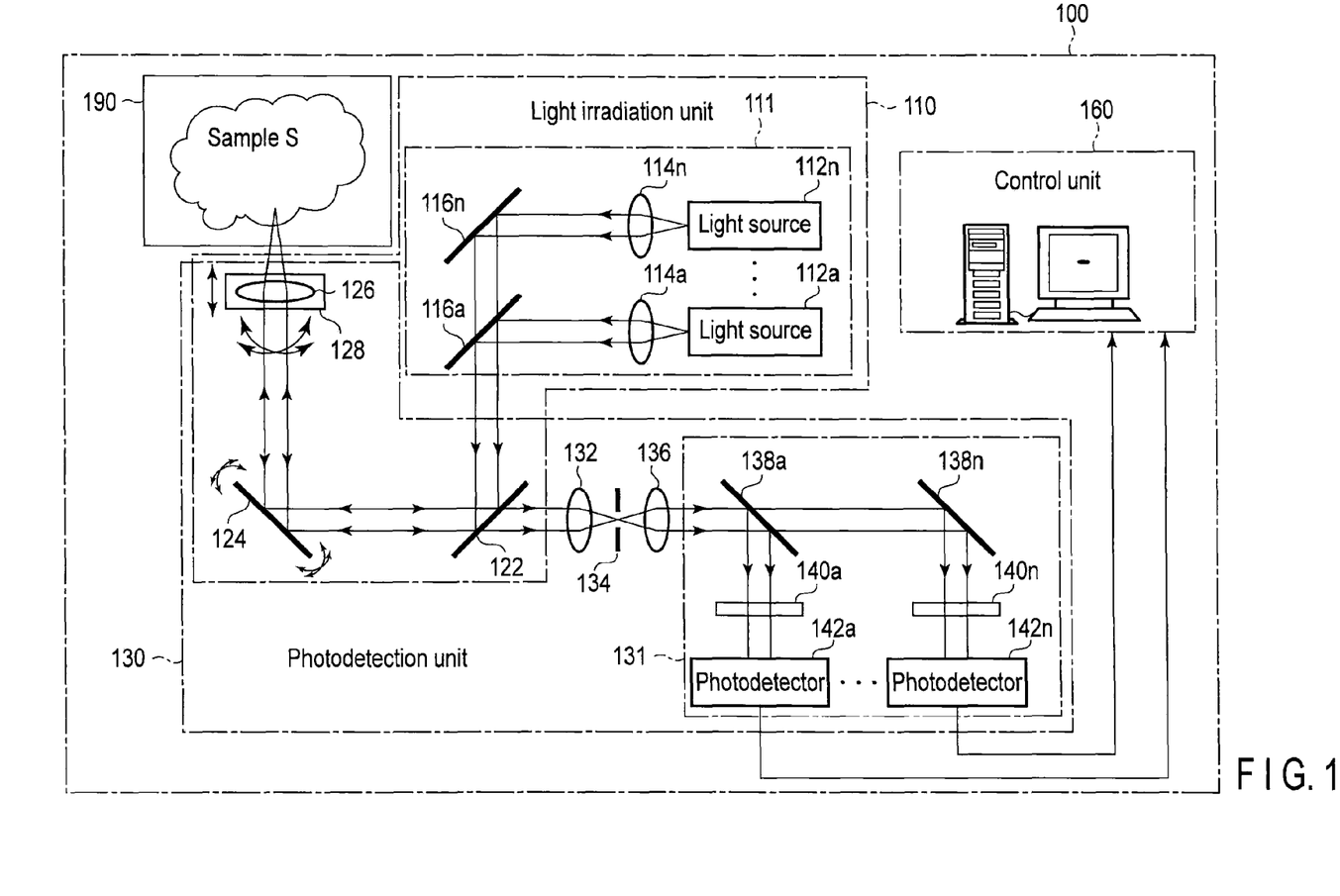
FIG. 1 is a schematic block diagram showing an image analysis apparatus according to an embodiment of the present invention.

FIG. 1 schematically shows an image analysis apparatus according to an embodiment of the present invention. This image analysis apparatus is configured based on a confocal scanning optical microscope required to observe fluorescence of a sample.

As shown in FIG. 1, an image analysis apparatus 100 includes a light irradiation unit 110 to irradiate a sample S with excitation light, a photodetection unit 130 to detect light emitted from a measurement point in the sample S, a control unit 160 to execute control required for image analysis, and a sample stage 190 to support the sample S.

The sample S is stored in a sample container such as a microplate or slide glass, and is placed on the sample stage 190. The sample stage 190 supports the sample S to be movable in, for example, horizontal directions (x and y directions) and a height direction (z direction) with respect to the light irradiation unit 110 and photodetection unit 130. For example, the sample stage 190 includes three stepping motors, output shafts of which are perpendicular to each other, and can move the sample S in the x, y, and z directions using these stepping motors.

The image analysis apparatus 100 is of a multi-light irradiation/multi-light detection type. For this reason, the light irradiation unit 110 includes n-channel light source systems 111, and the photodetection unit 130 includes n-channel detection systems 131 accordingly. The n-channel detection systems 131 respectively detect fluorescent rays generated by excitation light rays emitted from the n-channel light source systems 111. N channels include channel 1, channel 2, ..., channel n. The channels are different depending on types of excitation light rays.

The n-channel light source systems 111 of the light irradiation unit 110 include light sources 112a, ..., 112n, collimator lenses 114a, ..., 114n, and dichroic mirrors 116a, ..., 116n. The light sources 112a, ..., 112n emit excitation light rays required to excite fluorescent pigments contained in the sample S and to emit light rays (fluorescent rays) from the sample S. The excitation light rays emitted by the light sources 112a, ..., 112n have different wavelengths in correspondence with types of fluorescent pigments contained in the sample S. The light sources 112a, ..., 112n include, for example, laser light sources having oscillation wavelengths that match the fluorescent pigments in the sample S. The collimator lenses 114a, ..., 114n respectively collimate the excitation light rays emitted by the light sources 112a, ..., 112n. The dichroic mirrors 116a, ..., 116n respectively reflect the excitation light rays that have passed through the collimator lenses 114a, 114n in the same direction. The dichroic mirrors 116a, ..., 116n allow excitation light rays that come from the upper side of FIG. 1 to transmit through them, and reflect excitation light rays that come from the right side of FIG. 1. As a result, the excitation light rays of different wavelengths, which are respectively emitted from the light sources 112a, ..., 112n, are combined into a single beam after they passed through the dichroic mirror 116a. Since the dichroic mirror 116n need not transmit excitation light through it, it may be replaced by a simple mirror.

The light irradiation unit 110 further includes a dichroic mirror 122, galvano mirror 124, objective lens 126, and objective lens driving mechanism 128. The dichroic mirror 122 reflects the excitation light coming from the light source systems 111 toward the galvano mirror 124, and allows fluorescence emitted by the sample S to transmit through it. The galvano mirror 124 reflects the excitation light toward the objective lens 126, and changes its reflection direction. The objective lens 126 converges the excitation light to irradiate a measurement point in the sample S with the converged light, and fetches light from the measurement point in the sample S. The objective lens 126 having a large NA (Numerical Aperture) is used so as to form a very small confocal region (measurement point). The size of the confocal region obtained by this lens defines nearly a cylindrical shape having a diameter of about 0.6 μm and a length of about 2 μm. The galvano mirror 124 configures an x-y scanning mechanism to scan the measurement point in the x and y directions. The x-y scanning mechanism may be configured using an AOM (Acousto-Optical Modulator), polygonal mirror, hologram scanner, and the like in addition to the galvano mirror. The objective lens driving mechanism 128 moves the objective lens 126 along an optical axis. As a result, the measurement point is moved in the z direction. That is, the objective lens driving mechanism 128 configures a z scanning mechanism to scan the measurement point in the z direction.

The photodetection unit 130 shares the objective lens 126, galvano mirror 124, and dichroic mirror 122 with the light irradiation unit 110. The photodetection unit 130 further includes a converging lens 132, pinhole 134, and collimator lens 136. The converging lens 132 converges light that has transmitted through the dichroic mirror 122. The pinhole 134 is arranged at a focal point of the converging lens 132. That is, the pinhole 134 is located at a position conjugate with the measurement point in the sample S, and allows only light coming from the measurement point to pass through it. The collimator lens 136 collimates the light that has passed through the pinhole 134. The light that has passed through the collimator lens 136 enters the n-channel detection systems 131.

The n-channel detection systems 131 include dichroic mirrors 138a, ..., 138n, fluorescent filters 140a, ..., 140n, and photodetectors 142a, ..., 142n.

The dichroic mirrors 138a, ..., 138n respectively selectively reflect light rays of wavelengths near a fluorescence wavelength range that are generated from the sample S by the excitation light rays from the light sources 112a, ..., 112n. The dichroic mirror 138n may be replaced by a simple mirror since it need not transmit light through it. The fluorescent filters 140a, ..., 140n cut off light rays of unwanted wavelength components from the light rays reflected by the dichroic mirrors 138a, ..., 138n, and allow only fluorescent rays generated by the excitation light rays from the light sources 112a, 112n to selectively transmit through them. The fluorescent rays transmitted through the fluorescent filters 140a, ..., 140n respectively enter the photodetectors 142a, ..., 142n. The photodetectors 142a, ..., 142n output signals corresponding to intensities of incoming light rays. That is, the photodetectors 142a, ..., 142n output fluorescent intensity signals from the measurement point in the sample S.

The control unit 160 is configured by, for example, a personal computer. The control unit 160 executes acquisition/storage/display processes of a fluorescent image of an observation region of the sample S, input waiting processes of a setting of an analysis region, that of a sub-analysis region, that of a moving amount of the sub-analysis region, and the like, and image analysis processing (calculations of correlation values, estimation of a molecular number/diffusion time, and the like). The control unit 160 controls the galvano mirror 124 as the x-y scanning mechanism, the objective lens driving mechanism 128 as the z scanning mechanism, the sample stage 190, and the like.

Figure 2:
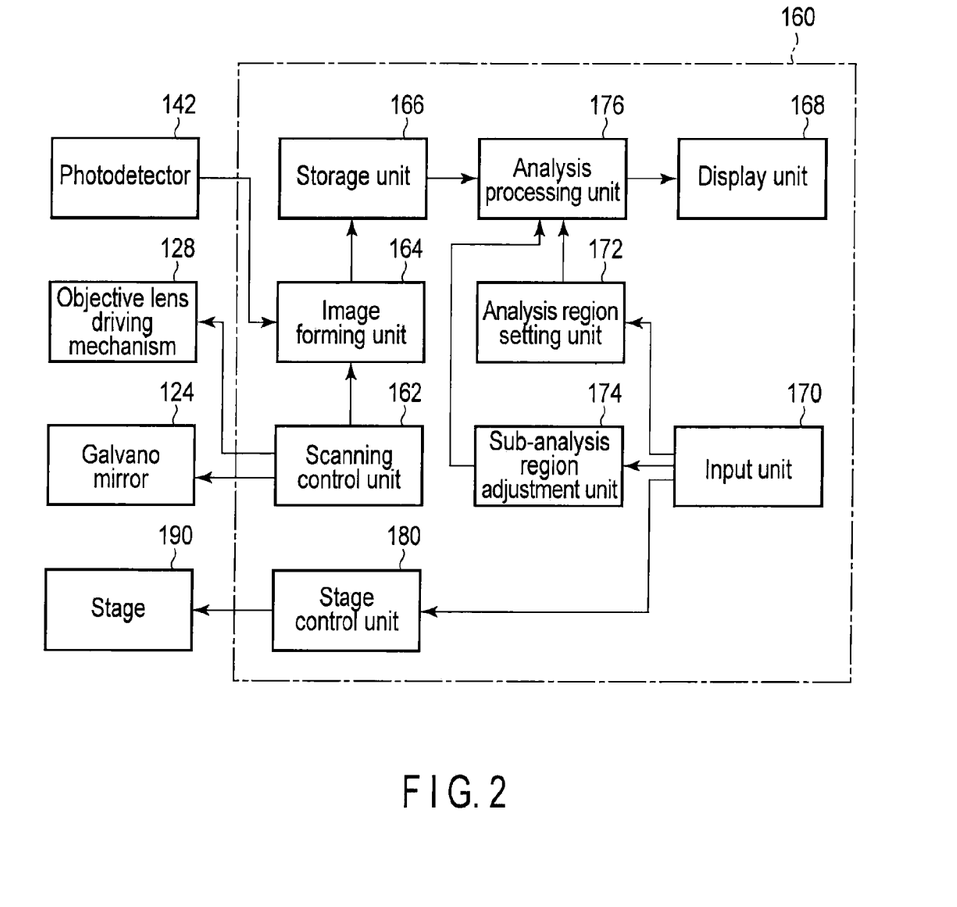
FIG. 2 is a block diagram showing functional blocks of a control unit shown in FIG. 1.

FIG. 2 shows a functional block diagram of the control unit shown in FIG. 1. As shown in FIG. 2, the control unit 160 includes a scanning control unit 162, image forming unit 164, storage unit 166, display unit 168, input unit 170, analysis region setting unit 172, sub-analysis region adjustment unit 174, analysis processing unit 176, and stage control unit 180. The scanning control unit 162, image forming unit 164, storage unit 166, and stage control unit 180, and the aforementioned galvano mirror 124, objective lens driving mechanism 128, sample stage 190, and photodetectors 142 configure an image acquisition unit.

The scanning control unit 162 controls the galvano mirrors 124 so as to raster-scan the irradiation position of excitation light with respect to the sample S at the acquisition timing of a fluorescent image of the sample S. The scanning control unit 162 controls the objective lens driving mechanism 128 so as to z-scan the irradiation position of excitation light with respect to the sample S if necessary. The image forming unit 164 forms a fluorescent image of the sample S based on pieces of information of excitation light irradiation positions input from the scanning control unit 162, and output signals from the photodetectors 142a, . . . , 142n. Thus, the fluorescent image is acquired. The storage unit 166 stores the fluorescent image formed by the image forming unit 164. The display unit 168 displays the fluorescent image and analysis processing result of the sample S. The input unit 170 includes, for example, a mouse and keyboard, and configures a GUI in cooperation with the display unit 168. This GUI is used to set an observation region, analysis region, sub-analysis region, and the like. The stage control unit 180 controls the sample stage 190 according to input information from the input unit 170, so as to set, for example, an observation region. The analysis region setting unit 172 sets an analysis region according to input information from the input unit 170. The sub-analysis region adjustment unit 174 sets a sub-analysis region smaller than the analysis region according to input information from the input unit 170. The sub-analysis region adjustment unit 174 intermittently moves the sub-analysis region in increments of a pixel interval over the entire analysis region. The analysis processing unit 176 executes correlation analysis using data of pixels in the sub-analysis region every time sub-analysis region is moved, and estimates at least a molecular number or diffusion constant of the sub-analysis region. Also, the analysis processing unit 176 forms a molecular number or diffusion constant image by mapping the estimated molecular numbers or diffusion constants. Furthermore, the analysis processing unit 176 executes extended calculations of the estimated molecular numbers or diffusion constants using an extension function having a two- or three-dimensional distribution to obtain the extended molecular numbers or extended diffusion constants, and forms an extended molecular number or extended diffusion constant image by mapping the extended molecular numbers or extended diffusion constants. Moreover, the analysis processing unit 176 converts the extended molecular number or extended diffusion constant image to the same image size as the analysis region using pieces of position information of the extended molecular numbers or extended diffusion constants as weighting coefficients. Details of the processing of the analysis processing unit 176 will be described later.

In FIG. 1, a measurement point in the sample S is irradiated with excitation light rays emitted by the light sources 112a, . . . , 112n via the collimator lenses 114a, . . . , 114n, dichroic mirrors 116a, . . . , 116n, dichroic mirror 122, galvano mirror 124, and objective lens 126. The measurement point irradiated with the excitation light rays is raster-scanned by the galvano mirror 124 in the x and y directions, and is also z-scanned by the objective lens driving mechanism 128 while being raster-scanned, if necessary. The measurement point is scanned over the entire observation region. The sample S that has received the excitation light rays emits fluorescence from the measurement point. Light rays (containing unwanted reflected light rays and the like in addition to the fluorescence) from the sample S reach the pinhole 134 via the objective lens 126, galvano mirror 124, dichroic mirror 122, and converging lens 132. Since the pinhole 134 is located at a position conjugate with the measurement point, only light rays coming from the measurement point in the sample S pass through the pinhole 134. The light rays that have passed through the pinhole 134, that is, those coming from the measurement point in the sample S enter the n-channel detection systems 131 via the collimator lens 136. The light rays that have entered the n-channel detection systems 131 are separated (that is, spectrally separated) by the dichroic mirrors 138a, . . . , 138n according to their wavelengths, and unwanted components are removed by the fluorescent filters 140a, . . . , 140n. As a result, only fluorescent rays generated by the excitation light rays from the light sources 112a, . . . , 112n respectively enter the photodetectors 142a, . . . , 142n. The photodetectors 142a, . . . , 142n respectively output fluorescent intensity signals indicating intensities of the incoming light rays, that is, the fluorescent rays emitted from the measurement point in the sample S. These fluorescent intensity signals are input to the image forming unit 164. The image forming unit 164 processes the input fluorescent intensity signals in synchronism with position information of the x and y directions (and z direction) to form a fluorescent image of the observation region in the sample S. The formed fluorescent image is saved in the storage unit 166. The fluorescent image saved in the storage unit 166 is displayed intact on the display unit 168, or it is processed by the analysis processing unit 176, and the analysis processing result is displayed on the display unit 168.

[Spatial Correlation Calculation Formula]

The fluorescent image of the observation region is defined by a plurality of pixels having a plurality of time-serially acquired data. Each measurement point has a spatial spread in the x, y, and z directions in practice, and each pixel has a size corresponding to this spatial spread of the measurement point. When the observation region is a two-dimensional region, the fluorescent image is a two-dimensional image on which pixels each having a size in the x and y directions are arranged two-dimensionally. On the other hand, when the observation region is a three-dimensional region, the fluorescent image is a three-dimensional image on which pixels each having a size in the x, y, and z directions are arranged three-dimensionally. From another viewpoint, the three-dimensional image is formed by a plurality of frames of two-dimensional images having different z positions.

Figure 3:
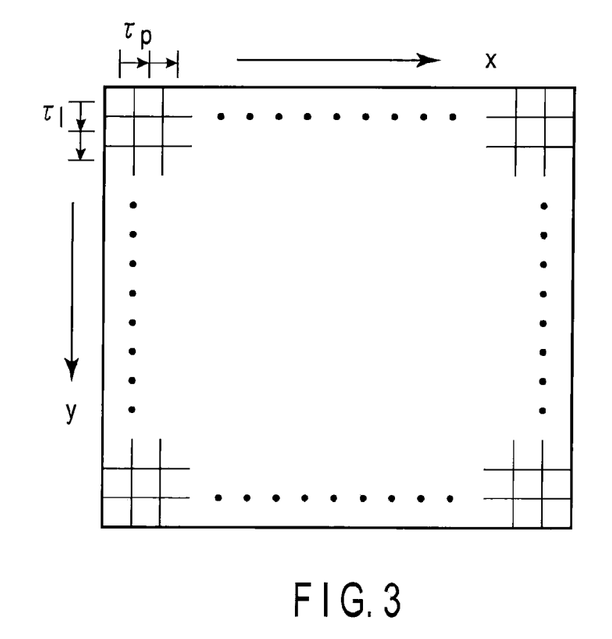
FIG. 3 is a view showing an example of a fluorescent image as a two-dimensional image.

FIG. 3 shows an example of a two-dimensional image. In FIG. 3, $\tau_p$ is an acquisition time difference (pixel time) between a certain pixel and the next pixel that neighbors that pixel. That is, the pixel time $\tau_p$ is a time required to acquire data of one pixel. Also, $\tau_l$ is an acquisition time difference (line time) between a first pixel of a certain line and that of the next line. That is, the line time $\tau_l$ means a time required to scan one line.

Formula (1) below represents a spatial autocorrelation calculation formula used in RICS analysis for a two-dimensional image. Formula (1) is an example of an autocorrelation calculation formula of channel 1.

$$G_{sa}(\xi, \psi) = \frac{\sum I_1(x, y) * I_1(x+\xi, y+\psi)/M_{11}}{(\sum I_1(x, y)/M_1)^2} \quad (1)$$

where $G_{sa}$ is a spatial autocorrelation value of the RICS, $I_1$ is fluorescent intensity data (data of a pixel) of channel 1, x and y are spatial coordinates of a measurement point, $\xi$ and $\psi$ are change amounts of the spatial coordinates from the measurement point, $M_{11}$ is a product-sum calculation count of data of channel 1, and $M_1$ is the total number of data of channel 1.

Formula (2) below represents a spatial cross-correlation calculation formula used in RICS analysis used for a two-dimensional image. Formula (2) is an example of a cross-correlation calculation formula of channels 1 and 2.

$$G_{sc}(\xi, \psi) = \frac{\sum I_1(x, y) * I_2(x+\xi, y+\psi)/M_{12}}{(\sum I_1(x, y)/M_1) \cdot (\sum I_2(x, y)/M_2)} \quad (2)$$

where $G_{sc}$ is a spatial cross-correlation value of the RICS, $I_1$ is fluorescent intensity data (data of a pixel) of channel 1, $I_2$ is fluorescent intensity data (data of a pixel) of channel 2, x and y are spatial coordinates of a measurement point, $\xi$ and $\psi$ are change amounts of the spatial coordinates from the measurement point, $M_{12}$ is a product-sum calculation count of data of channels 1 and 2, $M_1$ is the total number of data of channel 1, and $M_2$ is the total number of data of channel 2.

Formulas (3) below represent fitting formulas used in RICS analysis for a two-dimensional image.

$$G_s(\xi, \psi) = S(\xi, \psi) * G(\xi, \psi) \quad (3)$$

$$S(\xi, \psi) = \exp\left(-\frac{\frac{1}{2} * \left[\left(\frac{2\xi\delta_r}{W_0}\right)^2 + \left(\frac{2\psi\delta_r}{W_0}\right)^2\right]}{\left(1 + \frac{4D(\tau_p\xi + \tau_l\psi)}{W_0^2}\right)}\right)$$

$$G(\xi, \psi) = \frac{1}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_Z^2}\right)^{-1/2}\right)$$

where $G_s$ is a spatial correlation value (spatial autocorrelation value $G_{sa}$ or spatial cross-correlation value $G_{sc}$) of the RICS, S is the influence of a scan in the RICS analysis, G is the influence of a time delay in the RICS analysis, D is a diffusion constant, $\delta_r$ is a pixel size, N is a molecular number, $\xi$ and $\psi$ are change amounts of spatial coordinates from a measurement point, $W_0$ is a radius of an excitation laser beam in the horizontal direction, $W_Z$ is a radius of the excitation laser beam in the vertical direction, $\tau_p$ is a pixel time, and $\tau_l$ is a line time.

Figure 4:
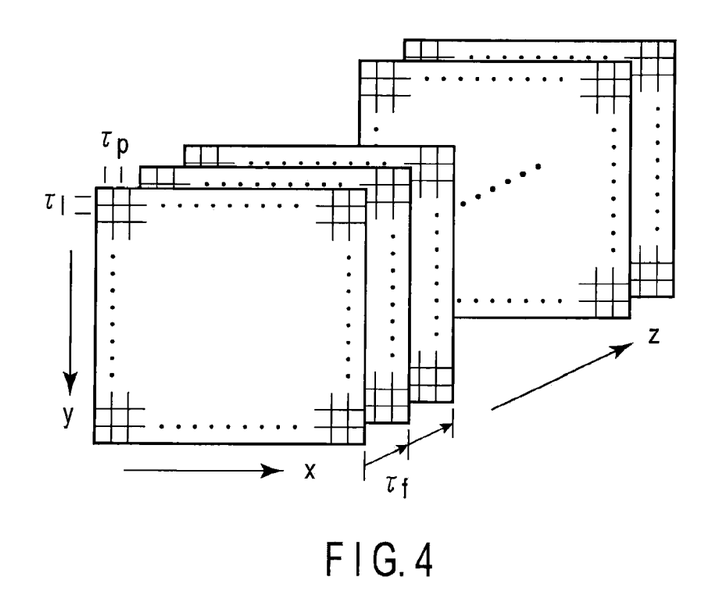
FIG. 4 is a view showing an example of a fluorescent image as a three-dimensional image.

FIG. 4 shows an example of a three-dimensional image. In FIG. 4, $\tau_p$ is a pixel time, $\tau_l$ is a line time, and $\tau_f$ is an acquisition time difference (frame time) between a first pixel of a certain, frame and that of the next frame. That is, the frame time $\tau_f$ means a time required to scan one frame.

Formula (4) below represents a spatial autocorrelation calculation formula used in RICS analysis for a three-dimensional image. Formula (4) is an example of an autocorrelation calculation formula of channel 1.

$$G_{sa}(\xi, \psi, \eta) = \frac{\sum I_1(x, y, z) * I_1(x+\xi, y+\psi, z+\eta)/M_{11}}{(\sum I_1(x, y, z)/M_1)^2} \quad (4)$$

where $G_{sa}$ is a spatial autocorrelation value of the RICS, $I_1$ is fluorescent intensity data (data of a pixel) of channel 1, x, y, and z are spatial coordinates of a measurement point, $\xi$, $\psi$, and $\eta$ are change amounts of the spatial coordinates from the measurement point, $M_{11}$ is a product-sum calculation count of data of channel 1, and $M_1$ is the total number of data of channel 1.

Formula (5) below represents a spatial cross-correlation calculation formula used in RICS analysis used for a three-dimensional image. Formula (5) is an example of a cross-correlation calculation formula of channels 1 and 2.

$$G_{sc}(\xi, \psi, \eta) = \frac{\sum I_1(x, y, z) * I_2(x+\xi, y+\psi, z+\eta)/M_{12}}{(\sum I_1(x, y, z)/M_1) \cdot (\sum I_2(x, y, z)/M_2)} \quad (5)$$

where $G_{sc}$ is a spatial cross-correlation value of the RICS, $I_1$ is fluorescent intensity data (data of a pixel) of channel 1, $I_2$ is fluorescent intensity data (data of a pixel) of channel 2, x, y, and z are spatial coordinates of a measurement point, $\xi$, $\psi$, and $\eta$ are change amounts of the spatial coordinates from the measurement point, $M_{12}$ is a product-sum calculation count of data of channels 1 and 2, $M_1$ is the total number of data of channel 1, and $M_2$ is the total number of data of channel 2.

Formulas (6) below represent fitting formulas used in RICS analysis for a three-dimensional image.

$$G_s(\xi, \psi, \eta) = S(\xi, \psi, \eta) * G(\xi, \psi, \eta) \quad (6)$$

$$S(\xi, \psi, \eta) = \exp\left(-\frac{\frac{1}{2} * \left[\left(\frac{2\xi\delta_r}{W_0}\right)^2 + \left(\frac{2\psi\delta_r}{W_0}\right)^2 + \left(\frac{2\eta\delta_r}{W_0}\right)^2\right]}{\left(1 + \frac{4D(\tau_p\xi + \tau_l\psi + \tau_f\eta)}{W_0^2}\right)}\right)$$

$$G(\xi, \psi, \eta) = \frac{1}{N}\left(\left(1 + \frac{4D(\tau_p\xi + \tau_l\psi + \tau_f\eta)}{W_0^2}\right)^{-1} * \left(1 + \frac{4D(\tau_p\xi + \tau_l\psi + \tau_f\eta)}{W_Z^2}\right)^{-1/2}\right)$$

where $G_s$ is a spatial correlation value (spatial autocorrelation value $G_{sa}$ or spatial cross-correlation value $G_{sc}$) of the RICS, S is the influence of a scan in the RICS analysis, G is the influence of a time delay in the RICS analysis, D is a diffusion constant, $\delta_r$ is a pixel size, N is a molecular number, $\xi$, $\psi$, and $\eta$ are change amounts of spatial coordinates from a measurement point, $W_0$ is a radius of an excitation laser beam in the horizontal direction, $W_Z$ is a radius of the excitation laser beam in the vertical direction, $\tau_p$ is a pixel time, $\tau_l$ is a line time, and $\tau_f$ is a frame time.

[Measurement Sequence]

Figure 5:
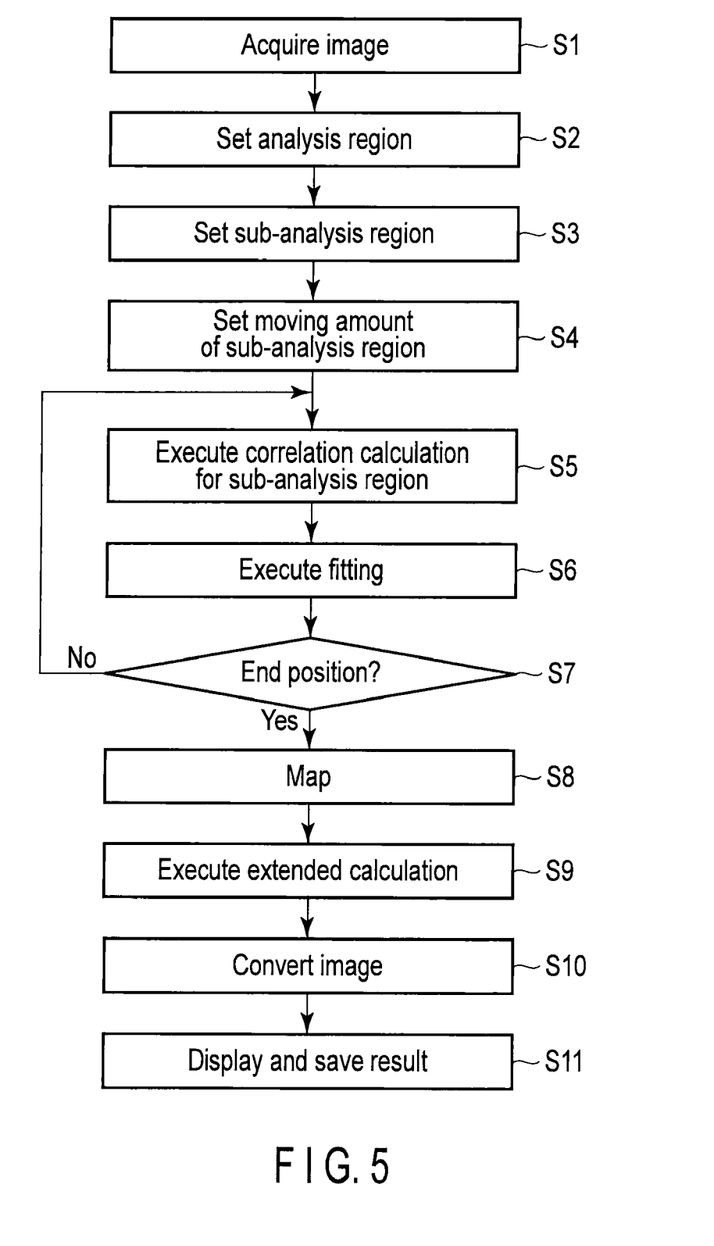
FIG. 5 is a flowchart of image analysis according to the embodiment of the present invention.

The image analysis sequence will be described below with reference to FIG. 5. Also, respective steps will be described with reference to FIGS. 6, 7, 8, 9, 10, and 11, as needed.

(Step S1)

A fluorescent image of an observation region of the sample S is acquired. The observation region is a two- or three-dimensional region, and the fluorescent image is a two- or three-dimensional image accordingly. Data of respective pixels of the fluorescent image are, for example, intensities of fluorescence emitted from corresponding measurement points.

(Step S2)

An analysis region is set for the fluorescent image of the observation region. The analysis region is a two-dimensional region for the two-dimensional observation region, and is normally a three-dimensional region for the three-dimensional observation region, but it may be a two-dimensional region. The analysis region may be a part of the observation region or may equal the observation region. For example, the analysis region is set to equal the observation region as a default in terms of an application.

(Step S3)

Figure 6:
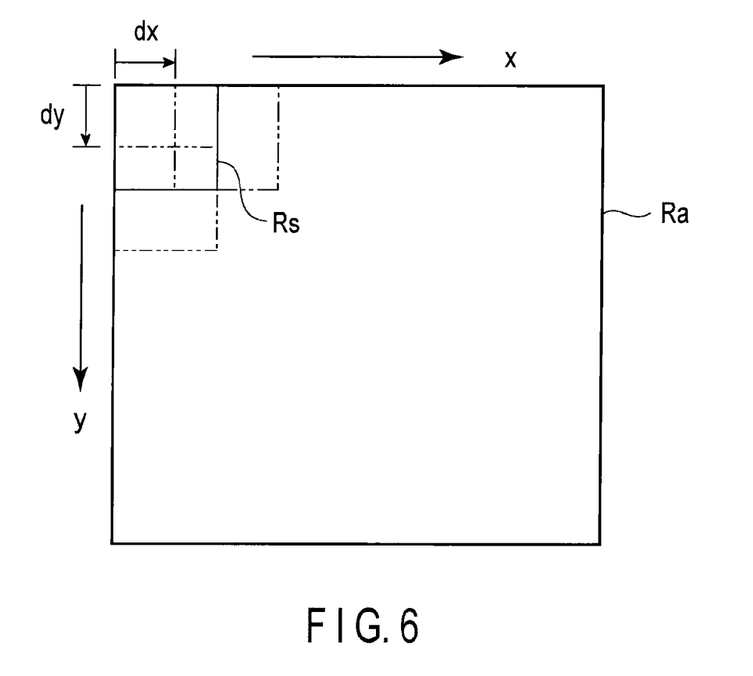
FIG. 6 is a view illustrating a sub-analysis region set for a two-dimensional analysis region.
Figure 7:
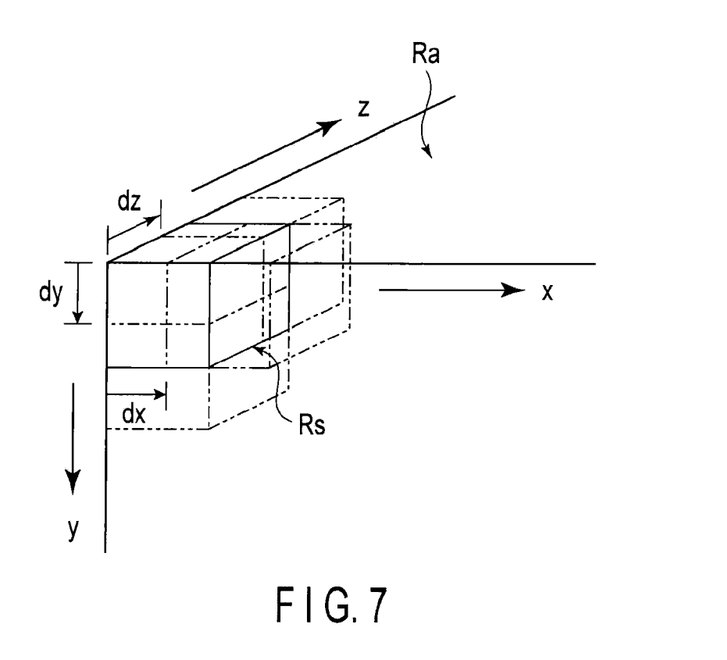
FIG. 7 is a view illustrating a sub-analysis region set for a three-dimensional analysis region.

A sub-analysis region smaller than the analysis region is set in the analysis region. For example, as shown in FIG. 6, a sub-analysis region Rs is a two-dimensional region for a two-dimensional analysis region Ra. Also, as shown in FIG. 7, a sub-analysis region Rs is a three-dimensional region for a three-dimensional analysis region Ra.

(Step S4)

A moving amount of the sub-analysis region is set. The sub-analysis region is intermittently moved in increments of a pixel interval over the entire analysis region. The sub-analysis region is set at an end of the analysis region as an initial position of movement. The sub-analysis region is moved within a range of the analysis region. The sub-analysis region is moved by a moving amount equal to or larger than one pixel.

For example, in the example shown in FIG. 6, the sub-analysis region is moved as follows to have an upper left position as an initial position. The sub-analysis region Rs is intermittently moved from the initial position by a moving amount dx in the x direction. This movement in the x direction is continued until the right end of the sub-analysis region Rs reaches the end of the analysis region Ra. Upon completion of the movement for one line in the x direction, the sub-analysis region Rs is moved to a position that is displaced by dy in the y direction from the initial position of that line. After that, the sub-analysis region Rs is similarly moved for one line in the x direction. Subsequently, every time the movement for one line of the sub-analysis region Rs in the x direction is complete, the sub-analysis region Rs is moved in the y direction. The movement in the y direction is continued until the lower end of the sub-analysis region Rs reaches the end of the analysis region Ra. Finally, the sub-analysis region Rs is moved for one line in the x direction, thus ending the movement.

In the example shown in FIG. 7, every time the aforementioned movements of the sub-analysis region Rs in the x and y directions are complete, the sub-analysis region Rs is moved by dz in the z direction, and the aforementioned movements in the x and y directions are repeated. The movement in the z direction is continued until the end of the sub-analysis region Rs reaches the end of the analysis region Ra. Finally, the sub-analysis region Rs is moved for one frame in the x and y directions, thus ending the movement.

(Steps S5 to S7)

The sub-analysis region is intermittently moved in increments of a pixel interval over the entire analysis region. Every time the sub-analysis region is moved, correlation analysis is executed for the sub-analysis region. That is, correlation analysis is executed for the sub-analysis region at the initial position and that after each movement.

(Step S5)

Correlation calculations are executed using data of pixels in the sub-analysis region. For a two-dimensional image, spatial autocorrelation values are calculated using the spatial autocorrelation calculation formula given by formula (1), and spatial cross-correlation values are calculated using the spatial cross-correlation calculation formula given by formula (2). For a three-dimensional image, spatial autocorrelation values are calculated using the spatial autocorrelation calculation formula given by formula (4), and spatial cross-correlation values are calculated using the spatial cross-correlation calculation formula given by formula (5).

Data of each pixel used in the correlation calculations may be data itself of that pixel, or a statistical value of data of a plurality of pixels including that pixel. The plurality of pixels may be, for example, a pixel of interest, and pixels that neighbor the pixel of interest. The statistical value may be, for example, any of an average value, maximum value, minimum value, relative difference, absolute difference, and relative ratio of data of pixels. The statistical value to be used is decided based on information to be obtained by the RICS analysis.

Data used in the correlation calculations may be a pixel time, line time, frame time, pixel positional relationship, pixel size, or statistical value associated with these values.

As for the correlation calculations, an image is reconstructed based on data of pixels, and the correlation calculations may be applied to the reconstructed image. For example, data of neighboring pixels are added to halve the number of data of pixels. Alternatively, data of one pixel is divided into a plurality of data. Originally, once an image is acquired, the number of data of pixels never increases. However, under the assumption that the intensity of an acquired pixel is spread to have a Gaussian distribution around the data of that pixel, data of a pixel that is not originally acquired is compensated for. Although the number of data of pixels is essentially not increased, the appearance can be improved.

(Step S6)

Fitting is applied to the correlation calculation results in step S5 to estimate at least a molecular number or diffusion time of the sub-analysis region. For a two-dimensional image, the fitting formulas given by formulas (3) are used. For a three-dimensional image, the fitting formulas given by formulas (6) are used.

More specifically, autocorrelation values $G_{sa}$ or cross-correlation values $G_{sc}$ for different delay times are respectively calculated using formulas (1) and (2) or formulas (4) and (5). From the relationship between the autocorrelation values $G_{sa}$ or cross-correlation values $G_{sc}$ and the delay times, a diffusion constant or molecular number is calculated using formulas (3) or (6).

In formulas (3) and (6), when a delay time is zero, ($\xi=0$, $\psi=0$) and ($\xi=0$, $\psi=0$, $\eta=0$), S=1, and an autocorrelation value $G_{sa}$ or cross-correlation value $G_{sc}$ is expressed by 1/N. Therefore, the molecular number can be calculated. By newly substituting this value in formulas (3) and (6), a diffusion constant corresponding to each delay time can be calculated.

While varying a diffusion constant D and molecular number N as unknowns, an appropriate diffusion constant D and molecular number N are calculated to minimize a difference between the correlation value $G_{sa}$ or $G_{sc}$ obtained as a measurement value and $G_s$ obtained as a theoretical value. In this manner, fitting using formulas (3) or (6) is to estimate the optimal molecular number or diffusion constant in the two- or three-dimensional observation region while varying the diffusion constant D and molecular number N.

The diffusion constant and diffusion time have a relationship given by formula (7) below between them. Therefore, a diffusion time can be calculated from the calculated diffusion constant.

$$\tau = W_0^2/4D \qquad (7)$$

(Step S7)

It is judged whether or not a position of the sub-analysis region is an end position. If the position of the sub-analysis region is not the end position, the sub-analysis region is moved to the next position, and the process returns to step S5. If the position of the sub-analysis region is the end position, the process advances to next step S8.

Upon completion of step S7, a plurality of molecular numbers or diffusion constants at the respective positions of the sub-analysis region are obtained.

(Step S8)

Figure 8:
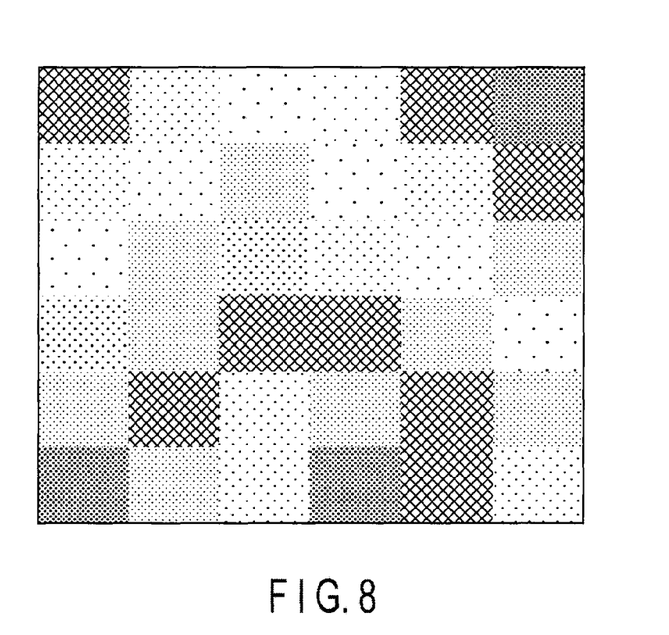
FIG. 8 shows a molecular number or diffusion constant image.

The molecular numbers or diffusion constants are mapped to form a molecular number or diffusion constant image. The molecular number or diffusion constant image is shown in FIG. 8.

(Step S9)

Figure 9:
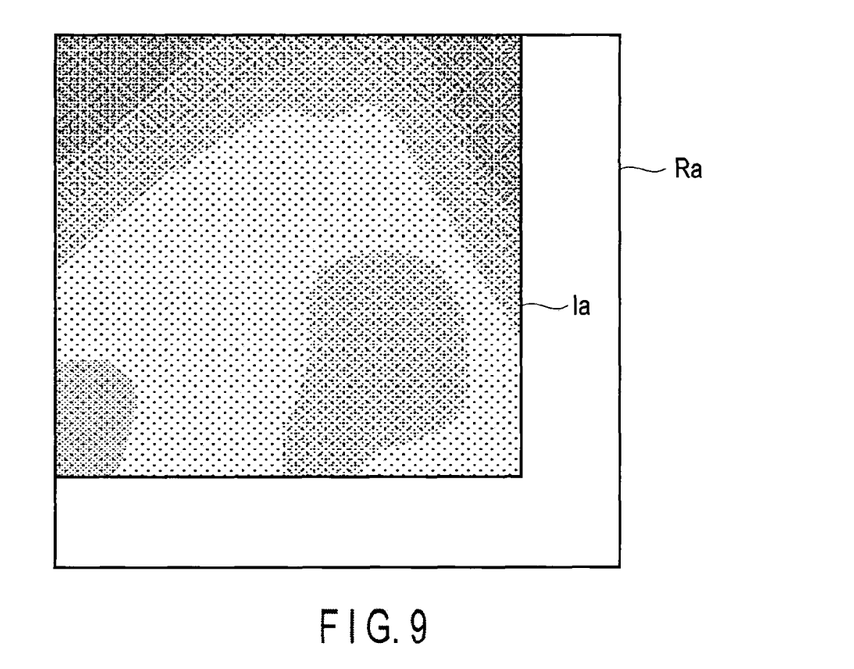
FIG. 9 shows an extended molecular number or extended diffusion constant image.

The molecular numbers or diffusion constants undergo extended calculations using an extension function having a two- or three-dimensional distribution, thereby obtaining the extended molecular numbers or extended diffusion constants. The extension function is not limited to this. For example, a Gaussian function may be used. The extended molecular numbers or extended diffusion constants are distributions of the molecular numbers or diffusion constants, and a distribution range is selected to be broader than the sub-analysis region. Also, the extended molecular numbers or extended diffusion constants are mapped to form an extended molecular number or extended diffusion constant image. The extended molecular number or extended diffusion constant image is shown in FIG. 9. In this manner, by applying the extended calculations to the molecular numbers or diffusion constants, the image with a smoother luminance change than the image shown in FIG. 8 can be obtained.

For example, in the example of FIG. 6, when the analysis region Ra has an image size of 256 pixels×256 pixels, the sub-analysis region Rs has an image size of 64 pixels×64 pixels, and the moving amounts dx and dy of the sub-analysis region Rs are respectively dx=1 pixel and dy=1 pixel, 192×192 molecular numbers or diffusion constants are obtained. As a result, an extended molecular number or extended diffusion constant image Ia has an image size of 192 pixels×192 pixels, which are smaller than 256 pixels×256 pixels as the image size of the analysis region Ra.

In consideration of comparison and examination of the extended molecular number or extended diffusion constant image Ia with an original image of the analysis region Ra, it is desirable that pieces of spatial position information between these images are matched. That is, it is desirable that the image size of the extended molecular number or extended diffusion constant image Ia equals that of the original image of the analysis region Ra.

(Step S10)

The extended molecular number or extended diffusion constant image is converted into the same image size as the analysis region using pieces of position information of the extended molecular numbers or extended diffusion constants as weighting coefficients.

Figure 10:
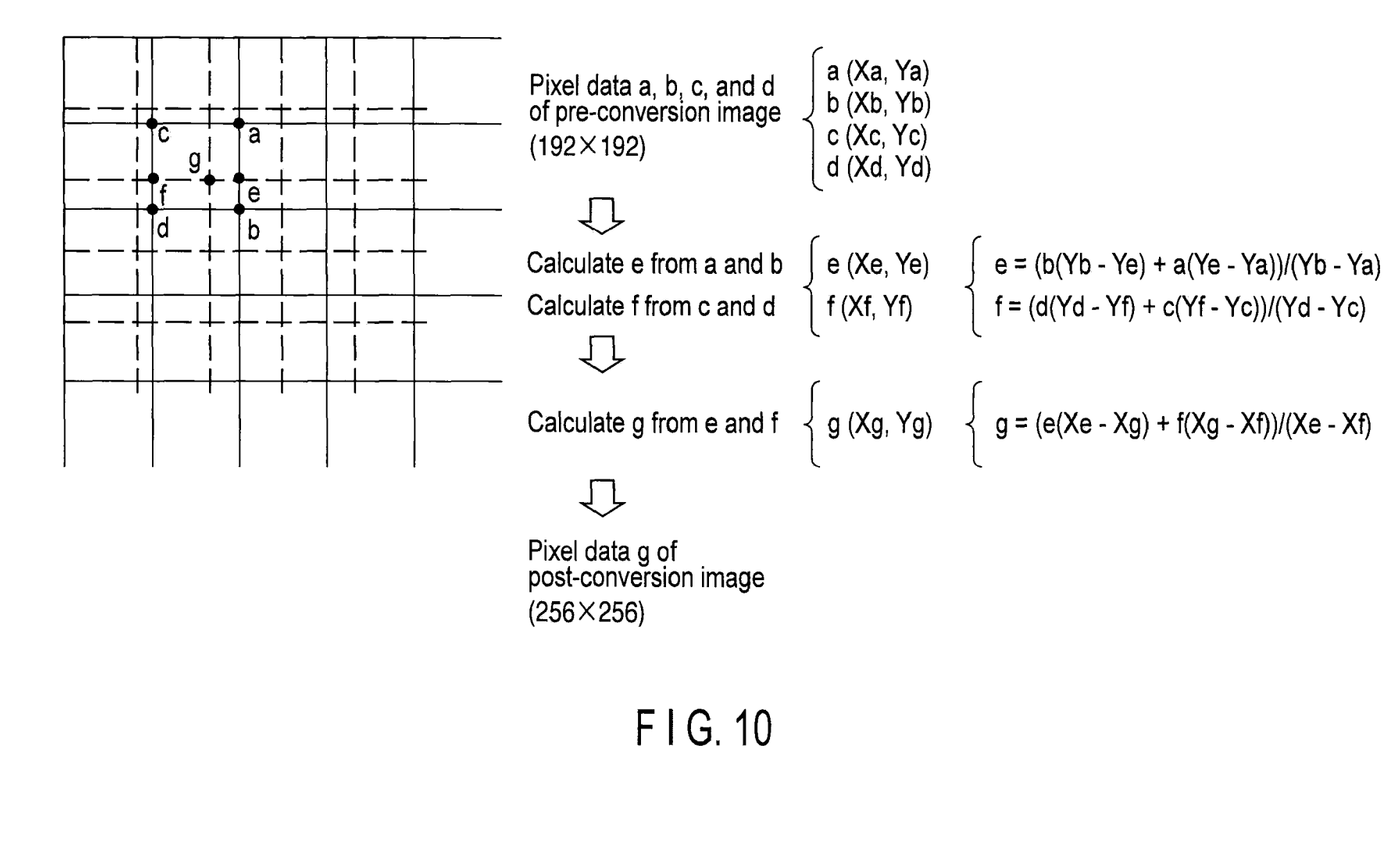
FIG. 10 is a view showing conversion of coordinate data between a pre-conversion image and post-conversion image.

For example, in the example shown in FIG. 9, the extended molecular number or extended diffusion constant image Ia is changed from an image size of 192×192 to that of 256×256. In the following description, the image having the image size of 192×192 will be referred to as a pre-conversion image, and that having the image size of 256×256 will be referred to as a post-conversion image. FIG. 10 shows coordinate data conversion between the pre-conversion and post-conversion images.

As shown in FIG. 10, let $a(Xa, Ya)$, $b(Xb, Yb)$, $c(Xc, Yc)$, and $d(Xd, Yd)$ respectively be coordinates of pixel data a, b, c, and d located at four corners of a unit square of coordinates of the pre-conversion image. Also, of points at which vertical axes of the pre-conversion image and horizontal axes of the post-conversion image intersect, let $e(Xe, Ye)$ be coordinates of a point that is located between $a(Xa, Ya)$ and $b(Xb, Yb)$ and $f(Xf, Yf)$ be coordinates of a point that is located between $c(Xc, Yc)$ and $d(Xd, Yd)$. Furthermore, let $g(Xg, Yg)$ be coordinates of the post-conversion image surrounded by $a(Xa, Ya)$, $b(Xb, Yb)$, $c(Xc, Yc)$, and $d(Xd, Yd)$.

From a and b, pixel data e at $e(Xe, Ye)$ is calculated. The pixel data e is calculated by $e=(b(Yb-Ye)+a(Ye-Ya))/(Yb-Ya)$. Also, from c and d, pixel data if at $f(Xf, Yf)$ is calculated. The pixel data if is calculated by $f=(d(Yd-Yf)+c(Yf-Yc))/(Yd-Yc)$.

From e and f, pixel data g at $g(Xg, Yg)$ is calculated. The pixel data g is calculated by $g=(e(Xe-Xg)+f(Xg-Xf))/(Xe-Xf)$.

Figure 11:
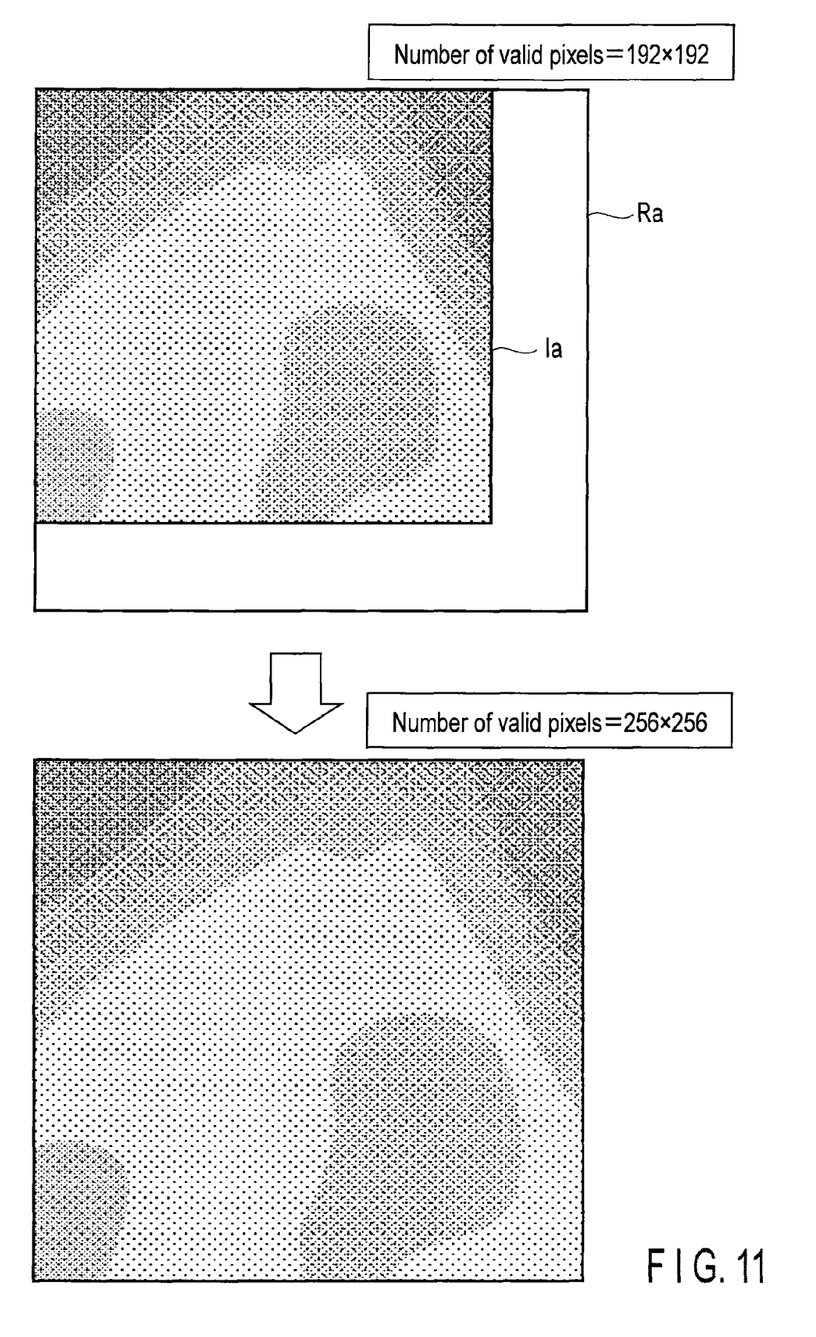
FIG. 11 is a view showing the pre-conversion image and post-conversion image.

By applying this conversion to all pixel data of the pre-conversion image, the post-conversion image having the image size of 256×256 can be obtained. The pre-conversion image and post-conversion image is shown in FIG. 11.

(Step S11)

The molecular number or diffusion constant image or the extended molecular number or extended diffusion constant image is displayed and saved.

REFERENCE SIGNS LIST

100 . . . image analysis apparatus, 110 . . . light irradiation unit, 112a, . . . , 112n . . . light source, 114a, . . . , 114n . . . collimator lens, 116a, . . . , 116n . . . dichroic mirror, 122 . . . dichroic mirror, 124 . . . galvano mirror, 126 . . . objective lens, 128 . . . objective lens driving mechanism, 130 . . . photodetection unit, 132 . . . converging lens, 134 . . . pinhole, 136 . . . collimator lens, 138a, . . . , 138n . . . dichroic mirror, 140a, . . . , 140n . . . fluorescent filter, 142a, . . . , 142n . . . photodetector, 160 . . . control unit, 162 . . . scanning control unit, 164 . . . image forming unit, 166 . . . storage unit, 168 . . . display unit, 170 . . . input unit, 172 . . . analysis region setting unit, 174 . . . sub analysis region adjustment unit, 176 . . . analysis processing unit, 180 . . . stage control unit, 190 . . . sample stage.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image analysis method comprising:
    acquiring an image of an observation region including a plurality of pixels respectively having a plurality of time-serially acquired data;
    setting an analysis region on the image of the observation region;
    setting a sub-analysis region smaller than the analysis region;
    intermittently moving the sub-analysis region in increments of a pixel interval over the entire analysis region;
    executing correlation analysis using data of pixels in the sub-analysis region every time the sub-analysis region is moved, so as to estimate at least a molecular number or a diffusion constant of the sub-analysis region; and
    forming a molecular number or diffusion constant image by mapping the molecular numbers or the diffusion constants.

2. The image analysis method according to claim 1, wherein the image of the observation region is a two-dimensional or three-dimensional image.

3. The image analysis method according to claim 1, wherein in the intermittently moving, the sub-analysis region is moved within a range of the analysis region.

4. The image analysis method according to claim 1, wherein in the intermittently moving, the sub-analysis region is moved by a moving amount of not less than one pixel.

5. The image analysis method according to claim 1, wherein in the correlation analysis, the correlation analysis is executed using a fluorescent intensity, a pixel time, a line time, a frame time, a pixel positional relationship, a pixel size, or a statistical value thereof.

6. The image analysis method according to claim 1, wherein in the correlation analysis, the correlation analysis is executed using one of an average value, a maximum value, a minimum value, a relative difference, and an absolute difference of the data.

7. The image analysis method according to claim 1, wherein in the correlation analysis, the correlation analysis is executed using reconstructed data obtained by reconstructing the data.

8. The image analysis method according to claim 1, wherein in the correlation analysis, correlation calculations are executed using formula (1) or formula (2) below, and fitting is executed using formulas (3) below for the correlation calculation results to estimate the molecular number or diffusion constant of a two-dimensional analysis region:

$$G_{sa}(\xi, \psi) = \frac{\sum I_1(x, y) * I_1(x+\xi, y+\psi)/M_{11}}{(\sum I_1(x, y)/M_1)^2} \quad (1)$$

where $G_{sa}$ is a spatial autocorrelation value of RICS, $I_1$ is fluorescent intensity data (data of a pixel) of channel 1, x and y are spatial coordinates of a measurement point, $\xi$ and $\psi$ are change amounts of the spatial coordinates from the measurement point, $M_{11}$ is a product-sum calculation count of data of channel 1, and $M_1$ is the total number of data of channel 1, $$G_{sc}(\xi, \psi) = \frac{\sum I_1(x, y) * I_2(x+\xi, y+\psi)/M_{12}}{(\sum I_1(x, y)/M_1) \cdot (\sum I_2(x, y)/M_2)} \quad (2)$$

where $G_{sc}$ is a spatial cross-correlation value of the RICS, $I_1$ is fluorescent intensity data (data of a pixel) of channel 1, $I_2$ is fluorescent intensity data (data of a pixel) of channel 2, x and y are spatial coordinates of a measurement point, $\xi$ and $\psi$ are change amounts of the spatial coordinates from the measurement point, $M_{12}$ is a product-sum calculation count of data of channels 1 and 2, $M_1$ is the total number of data of channel 1, and $M_2$ is the total number of data of channel 2, $$G_s(\xi, \psi) = S(\xi, \psi) * G(\xi, \psi) \quad (3)$$

$$S(\xi, \psi) = \exp\left(-\frac{\frac{1}{2}*\left[\left(\frac{2\xi\delta_r}{W_0}\right)^2 + \left(\frac{2\psi\delta_r}{W_0}\right)^2\right]}{\left(1 + \frac{4D(\tau_p\xi + \tau_l\psi)}{W_0^2}\right)}\right)$$

$$G(\xi, \psi) = \frac{1}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_Z^2}\right)^{-1/2}\right)$$

where $G_s$ is a spatial correlation value of RICS, S is an influence of a scan in RICS analysis, G is an influence of a time delay in the RICS analysis, D is a diffusion constant, $\delta_r$ is a pixel size, N is a molecular number, $\xi$ and $\psi$ are change amounts of spatial coordinates from a measurement point, $W_0$ is a radius of an excitation laser beam in a horizontal direction, $W_Z$ is a radius of the excitation laser beam in a vertical direction, $\tau_p$ is a pixel time, and $\tau_l$ is a line time.

9. The image analysis method according to claim 1, wherein in the correlation analysis, correlation calculations are executed using formula (4) or formula (5) below, and fitting is executed using formulas (6) below for the correlation calculation results to estimate the molecular number or diffusion constant of a three-dimensional analysis region:

$$G_{sa}(\xi, \psi, \eta) = \frac{\sum I_1(x, y, z) * I_1(x+\xi, y+\psi, z+\eta)/M_{11}}{(\sum I_1(x, y, z)/M_1)^2} \quad (4)$$

where $G_{sa}$ is a spatial autocorrelation value of RICS, $I_1$ is fluorescent intensity data (data of a pixel) of channel 1, x, y, and z are spatial coordinates of a measurement point, $\xi$, $\psi$, and $\eta$ are change amounts of the spatial coordinates from the measurement point, $M_{11}$ is a product-sum calculation count of data of channel 1, and $M_1$ is the total number of data of channel 1, $$G_{sc}(\xi, \psi, \eta) = \frac{\sum I_1(x, y, z) * I_2(x+\xi, y+\psi, z+\eta)/M_{12}}{(\sum I_1(x, y, z)/M_1) \cdot (\sum I_2(x, y, z)/M_2)} \quad (5)$$

where $G_{sc}$ is a spatial cross-correlation value of RICS, $I_1$ is fluorescent intensity data (data of a pixel) of channel 1, $I_2$ is fluorescent intensity data (data of a pixel) of channel 2, x, y, and z are spatial coordinates of a measurement point, $\xi$, $\psi$, and $\eta$ are change amounts of the spatial coordinates from the measurement point, $M_{12}$ is a product-sum calculation count of data of channels 1 and 2, $M_1$ is the total number of data of channel 1, and $M_2$ is the total number of data of channel 2, $$G_s(\xi, \psi, \eta) = S(\xi, \psi, \eta) * G(\xi, \psi, \eta) \quad (6)$$

$$S(\xi, \psi, \eta) = \exp\left(-\frac{\frac{1}{2}*\left[\left(\frac{2\xi\delta_r}{W_0}\right)^2 + \left(\frac{2\psi\delta_r}{W_0}\right)^2 + \left(\frac{2\eta\delta_r}{W_0}\right)^2\right]}{\left(1 + \frac{4D(\tau_p\xi + \tau_l\psi + \tau_f\eta)}{W_0^2}\right)}\right)$$

$$G(\xi, \psi, \eta) = \frac{1}{N}\left(\left(1 + \frac{4D(\tau_p\xi + \tau_l\psi + \tau_f\eta)}{W_0^2}\right)^{-1} * \left(1 + \frac{4D(\tau_p\xi + \tau_l\psi + \tau_f\eta)}{W_Z^2}\right)^{-1/2}\right)$$

where $G_s$ is a spatial correlation value (spatial autocorrelation value $G_{sa}$ or spatial cross-correlation value $G_{sc}$) of RICS, S is an influence of a scan in RICS analysis, G is an influence of a time delay in the RICS analysis, D is a diffusion constant, $\delta_r$ is a pixel size, N is a molecular number, $\xi$, $\psi$, and $\eta$ are change amounts of spatial coordinates from a measurement point, $W_0$ is a radius of an excitation laser beam in a horizontal direction, $W_Z$ is a radius of the excitation laser beam in a vertical direction, $\tau_p$ is a pixel time, $\tau_l$ is a line time, and $\tau_f$ is a frame time.

10. The image analysis method according to claim 1, further comprising:
executing extended calculations of the molecular number or the diffusion constant using an extension function having a two-dimensional or three-dimensional distribution to obtain an extended molecular number or an extended diffusion constant; and forming an extended molecular number or extended diffusion constant image by mapping the extended molecular numbers or the extended diffusion constants.

11. The image analysis method according to claim 10, further comprising converting the extended molecular number or extended diffusion constant image into, an image size that is equal to that of the analysis region using pieces of position information of the extended molecular numbers or the extended diffusion constants as weighting coefficients.

12. The image analysis method according to claim 11, further comprising displaying the molecular number or diffusion constant image or the extended molecular number or extended diffusion constant image.

13. An image analysis apparatus comprising:

an image acquisition unit configured to acquire an image of an observation region including a plurality of pixels respectively having a plurality of time-serially acquired data;

an analysis region setting unit configured to set an analysis region on the image of the observation region;

a sub-analysis region adjustment unit configured to set a sub-analysis region smaller than the analysis region, and to intermittently move the sub-analysis region in increments of a pixel interval over the entire analysis region; and an analysis processing unit configured to execute correlation analysis using data of pixels in the sub-analysis region every time the sub-analysis region is moved, so as to estimate at least a molecular number or a diffusion constant of the sub-analysis region, and to form a molecular number or diffusion constant image by mapping the molecular numbers or the diffusion constants.

14. The image analysis apparatus according to claim 13, wherein the image of the observation region is a two-dimensional or three-dimensional image.

15. The image analysis apparatus according to claim 13, wherein the sub-analysis region adjustment unit moves the sub-analysis region within a range of the analysis region.

16. The image analysis apparatus according to claim 13, wherein the sub-analysis region adjustment unit moves the sub-analysis region by a moving amount of not less than one pixel.

17. The image analysis apparatus according to claim 13, wherein the analysis processing unit executes the correlation analysis using a fluorescent intensity, a pixel time, a line time, a frame time, a pixel positional relationship, a pixel size, or a statistical value thereof.

18. The image analysis apparatus according to claim 13, wherein the analysis processing unit executes the correlation analysis using one of an average value, a maximum value, a minimum value, a relative difference, and an absolute difference of the data.

19. The image analysis apparatus according to claim 13, wherein the analysis processing unit executes the correlation analysis using reconstructed data obtained by reconstructing the data.

20. The image analysis apparatus according to claim 13, wherein the analysis processing unit executes correlation calculations using formula (1) or formula (2) below, and executes fitting using formulas (3) below for the correlation calculation results to estimate the molecular number or diffusion constant of a two-dimensional analysis region:

$$G_{sa}(\xi, \psi) = \frac{\sum I_1(x, y) * I_1(x+\xi, y+\psi)/M_{11}}{(\sum I_1(x, y)/M_1)^2} \quad (1)$$

where $G_{sa}$ is a spatial autocorrelation value of RICS, $I_1$ is fluorescent intensity data (data of a pixel) of channel 1, x and y are spatial coordinates of a measurement point, $\xi$ and $\psi$ are change amounts of the spatial coordinates from the measurement point, $M_{11}$ is a product-sum calculation count of data of channel 1, and $M_1$ is the total number of data of channel 1, $$G_{sc}(\xi, \psi) = \frac{\sum I_1(x, y) * I_2(x+\xi, y+\psi)/M_{12}}{(\sum I_1(x, y)/M_1) \cdot (\sum I_2(x, y)/M_2)} \quad (2)$$

where $G_{sc}$ is a spatial cross-correlation value of RICS, $I_1$ is fluorescent intensity data (data of a pixel) of channel 1, $I_2$ is fluorescent intensity data (data of a pixel) of channel 2, x and y are spatial coordinates of a measurement point, $\xi$ and $\psi$ are change amounts of the spatial coordinates from the measurement point, $M_{12}$ is a product-sum calculation count of data of channels 1 and 2, $M_1$ is the total number of data of channel 1, and $M_2$ is the total number of data of channel 2, $$G_s(\xi, \psi) = S(\xi, \psi) * G(\xi, \psi) \quad (3)$$

$$S(\xi, \psi) = \exp\left(-\frac{\frac{1}{2} * \left[\left(\frac{2\xi\delta_r}{W_0}\right)^2 + \left(\frac{2\psi\delta_r}{W_0}\right)^2\right]}{\left(1 + \frac{4D(\tau_p\xi + \tau_l\psi)}{W_0^2}\right)}\right)$$

$$G(\xi, \psi) = \frac{1}{N}\left(\left(1 + \frac{4D(\tau_p\xi + \tau_l\psi)}{W_0^2}\right)^{-1} * \left(1 + \frac{4D(\tau_p\xi + \tau_l\psi)}{W_Z^2}\right)^{-1/2}\right)$$

where $G_s$ is a spatial correlation value of RICS, S is an influence of a scan in RICS analysis, G is an influence of a time delay in the RICS analysis, D is a diffusion constant, $\delta_r$ is a pixel size, N is a molecular number, $\xi$ and $\psi$ are change amounts of spatial coordinates from a measurement point, $W_0$ is a radius of an excitation laser beam in a horizontal direction, $W_Z$ is a radius of the excitation laser beam in a vertical direction, $\tau_p$ is a pixel time, and $\tau_l$ is a line time.

21. The image analysis apparatus according to claim 13, wherein the analysis processing unit executes correlation calculations using formula (4) or formula (5) below, and executes fitting using formulas (6) below for the correlation calculation results to estimate the molecular number or diffusion constant of a three-dimensional analysis region:

$$G_{sa}(\xi, \psi, \eta) = \frac{\sum I_1(x, y, z) * I_1(x+\xi, y+\psi, z+\eta)/M_{11}}{(\sum I_1(x, y, z)/M_1)^2} \quad (4)$$

where $G_{sa}$ is a spatial autocorrelation value of RICS, $I_1$ is fluorescent intensity data (data of a pixel) of channel 1, x, y, and z are spatial coordinates of a measurement point, $\epsilon$, $\psi$, and $\eta$ are change amounts of the spatial coordinates from the measurement point, $M_{11}$ is a product-sum calculation count of data of channel 1, and $M_1$ is the total number of data of channel 1, $$G_{sc}(\xi, \psi, \eta) = \frac{\sum I_1(x, y, z) * I_2(x+\xi, y+\psi, z+\eta)/M_{12}}{(\sum I_1(x, y, z)/M_1) \cdot (\sum I_2(x, y, z)/M_2)} \quad (5)$$

where $G_{sc}$ is a spatial cross-correlation value of RICS, $I_1$ is fluorescent intensity data (data of a pixel) of channel 1, $I_2$ is fluorescent intensity data (data of a pixel) of channel 2, x, y, and z are spatial coordinates of a measurement point, $\xi$, $\psi$, and $\eta$ are change amounts of the spatial coordinates from the measurement point, $M_{12}$ is a product-sum calculation count of data of channels 1 and 2, $M_1$ is the total number of data of channel 1, and $M_2$ is the total number of data of channel 2, $$G_s(\xi, \psi, \eta) = S(\xi, \psi, \eta) * G(\xi, \psi, \eta) \quad (6)$$

$$S(\xi, \psi, \eta) = \exp\left(-\frac{\frac{1}{2} * \left[\left(\frac{2\xi\delta_r}{W_0}\right)^2 + \left(\frac{2\psi\delta_r}{W_0}\right)^2 + \left(\frac{2\eta\delta_r}{W_0}\right)^2\right]}{\left(1 + \frac{4D(\tau_p\xi + \tau_l\psi + \tau_f\eta)}{W_0^2}\right)}\right)$$

$$G(\xi, \psi, \eta) = \frac{1}{N}\left(\left(1 + \frac{4D(\tau_p\xi + \tau_l\psi + \tau_f\eta)}{W_0^2}\right)^{-1} * \left(1 + \frac{4D(\tau_p\xi + \tau_l\psi + \tau_f\eta)}{W_Z^2}\right)^{-1/2}\right)$$

where $G_s$ is a spatial correlation value (spatial autocorrelation value $G_{sa}$ or spatial cross-correlation value $G_{sc}$) of RICS, S is an influence of a scan in RICS analysis, G is an influence of a time delay in the RICS analysis, D is a diffusion constant, $\delta_r$ is a pixel size, N is a molecular number, $\xi$, $\psi$, and $\eta$ are change amounts of spatial coordinates from a measurement point, $W_0$ is a radius of an excitation laser beam in a horizontal direction, $W_Z$ is a radius of the excitation laser beam in a vertical direction, $\tau_p$ is a pixel time, $\tau_l$ is a line time, and $\tau_f$ is a frame time.

22. The image analysis apparatus according to claim 13, wherein the analysis processing unit further executes extended calculations of the molecular number or the diffusion constant using an extension function having a two-dimensional or three-dimensional distribution to obtain an extended molecular number or an extended diffusion constant, and forms an extended molecular number or extended diffusion constant image by mapping the extended molecular numbers or the extended diffusion constants.

23. The image analysis apparatus according to claim 22, wherein the analysis processing unit further converts the extended molecular number or extended diffusion constant image into an image size that is equal to that of the analysis region using pieces of position information of the extended molecular numbers or the extended diffusion constants as weighting coefficients.

24. The image analysis apparatus according to claim 23, further comprising a display unit configured to display the molecular number or diffusion constant image or the extended molecular number or extended diffusion constant image.

\* \* \* \* \*